(12) United States Patent
Wolf et al.

(10) Patent No.: US 7,271,253 B1
(45) Date of Patent: Sep. 18, 2007

(54) SAFE PROCESS FOR THE PREPARATION OF BALSALAZIDE

(75) Inventors: Eckardt C. G. Wolf, Brantford (CA); Nageib Mohamed, Oakville (CA); Bhaskar Reddy Guntoori, Brantford (CA)

(73) Assignee: Apotex Pharmachem Inc., Brantford, Ontario (CA)

( * ) Notice: Subject to any disclaimer, the term of this patent is extended or adjusted under 35 U.S.C. 154(b) by 0 days.

(21) Appl. No.: 11/501,770

(22) Filed: Aug. 10, 2006

(51) Int. Cl.
*C07C 245/08* (2006.01)
*C07C 245/20* (2006.01)

(52) U.S. Cl. ..................... 534/564; 534/660

(58) Field of Classification Search ............... 534/564, 534/660
See application file for complete search history.

(56) References Cited

U.S. PATENT DOCUMENTS 4,412,992 A 11/1983 Chan
6,458,776 B1 * 10/2002 Ekwuribe et al. ........... 514/150

OTHER PUBLICATIONS

Shan, et al., Zhongguo Yaowu Huaxue Zazhi, Institute of Materia Medica, Peking Union Medical College, Beijing China, 2001, 11(2), 110-111.

Shi, et al., Zhongguo Yiyao Gongya Zazhi, Shanghai Institute of Pharmaceutical Industry, Shanghai, China, 2003, 34(11), 537-538.

Ullrich, et al., Decomposition of aromataic diazonium compounds, Thermochimica Acta, 1993, 225, 201-211.

Su, et al., Huaxue Gongye Yu Gongcheng (Tianjin, China), College of Chemistry and Chemical Eng., Donghua Univ., Shanghai, China, 2005, 22(4), 313-315.

Chai, et al., Huaxi Yaoxue Zazhi, Jiangsu Institute of Materia Medica, Nanjing, China, 2004, 19(6), 431-433.

* cited by examiner

*Primary Examiner*—Fiona T. Powers
(74) *Attorney, Agent, or Firm*—Ivor M. Hughes

(57) ABSTRACT

A process for the preparation of Balsalazide and its pharmaceutically acceptable salts wherein the reaction comprises:

a. the intermediate N-(4-aminobenzoyl)-β-alanine is converted to N-(4-ammoniumbenzoyl)-β-alanine sulfonate salt using a sulfonic acid in water,
b. the N-(4-ammoniumbenzoyl)-β-alanine sulfonate salt is treated with aqueous sodium nitrite solution at low temperature to generate N-(4-diazoniumbenzoyl)-β-alanine sulfonate salt,
c. the aqueous solution obtained is quenched with aqueous disodium salicylate to furnish Balsalazide disodium solution,
d. the solution is acidified to allow isolation of Balsalazide, and
e. optionally converting the Balsalazide to a pharmaceutically acceptable salt (such as disodium salt).

19 Claims, 4 Drawing Sheets

SAFE PROCESS FOR THE PREPARATION OF BALSALAZIDE

FIELD OF INVENTION

The present invention relates to an improved process for the manufacture of the known anti-inflammatory drug Balsalazide disodium (Colazal™).

BACKGROUND OF THE INVENTION

Balsalazide disodium (1) represents an effective gastrointestinal anti-inflammatory compound useful as a medicament for the treatment of diseases such as ulcerative colitis. It is delivered intact to the colon where it is cleaved by bacterial azoreduction thereby generating 5-aminosalicylic acid as the medicinally active component.

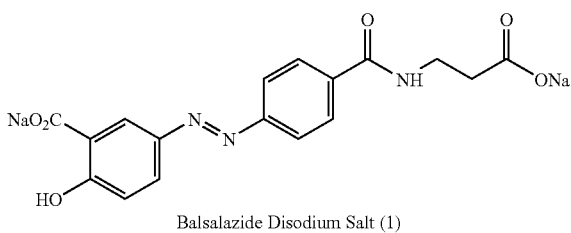

Balsalazide Disodium Salt (1)

To date, relatively few patents or literature articles have dealt with the preparation of Balsalazide or the disodium salt. For instance, U.S. Pat. No. 4,412,992 (Biorex, 1983) is the first patent that we uncovered that claims the compound Balsalazide and a strategy of how to prepare it which strategy is depicted in Scheme 1.

It is well-documented in the literature, for instance in Thermochimica Acta, 225, 201-211 (1993), that diazonium salts can be involved in serious accidents in their use. A possible cause of some of the diazonium salt related accidents is that, for one reason or another, an intermediate material appeared in crystalline form in the vessel of the reaction. As a result, a potentially severe drawback of the above processes occurs. Since the intermediate hydrochloride salt of 4-aminobenzoyl-β-alanine has poor solubility in water, it may pose a safety-risk in the subsequent diazotation reaction.

Also, it is well-known that certain diazonium salts possess high mechanical and heat sensitivity and that their decomposition goes through the liberation of non-condensable nitrogen gas which results in the possibility of runaway reactions and explosions. Obviously this safety consideration becomes more pertinent upon further scale-up.

Therefore, for commercial production of Balsalazide disodium, there was a need to develop a scalable and intrinsically better process.

SUMMARY OF THE INVENTION

According to one aspect of the invention, a more soluble salt of N-(4-aminobenzoyl)-β-alanine is provided which overcomes the use of the previous forms which were virtually insoluble in water. For example, even the mineral acid salts of N-(4-aminobenzoyl)-β-alanine examined, for instance the chloride, bromide, sulfate, hydrogensulfate, and phosphate salts and the free-base, were poorly soluble in water.

Thus, according to another aspect of the invention, a process for the manufacture of Balsalazide and its salts, for example the Balsalazide disodium salt, comprises:

Scheme 1:

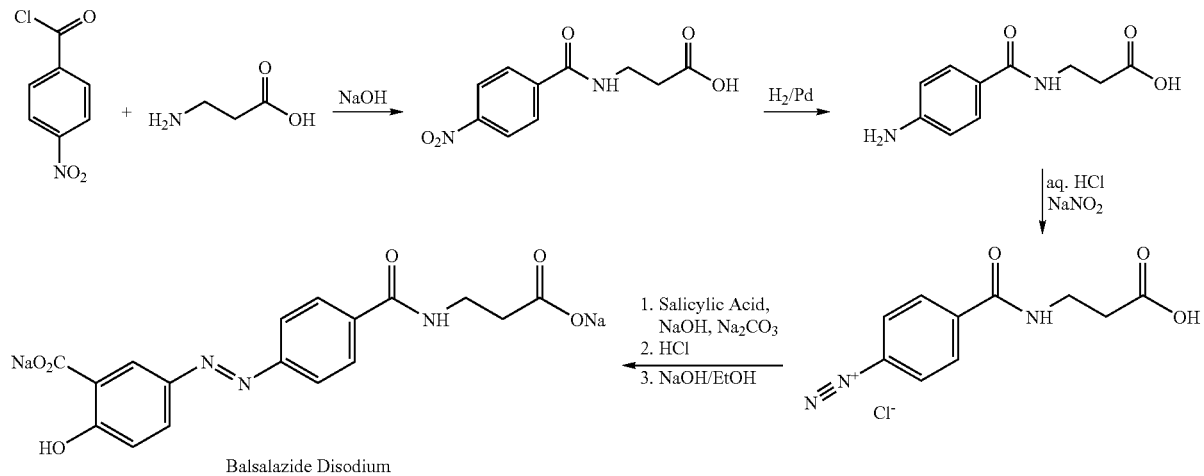

Optimization of this diazonium-based process is detailed in Shan et al., Zhongguo Yaowu Huaxue Zazhi, 11, 110 (2001) and Shi et al., Zhongguo Yiyao Gongye Zazhi, 34, 537 (2003).

Problems arise with the above strategy and the optimization process.

a. the intermediate N-(4-aminobenzoyl)-β-alanine is converted to N-(4-ammoniumbenzoyl)-β-alanine sulfonate salt using a sulfonic acid in water, b. the N-(4-ammoniumbenzoyl)-β-alanine sulfonate salt is treated with aqueous sodium nitrite solution at low temperature to generate N-(4-diazoniumbenzoyl)-β-alanine sulfonate salt, c. the aqueous solution obtained is quenched with aqueous disodium salicylate to furnish Balsalazide disodium solution, d. the solution is acidified to allow isolation of Balsalazide, and e. optionally converting the Balsalazide to a pharmaceutically acceptable salt (such as disodium salt).

Thus, according to another aspect of the invention, a process for the manufacture of Balsalazide and its salts, for example the Balsalazide disodium salt, comprises:

a. converting N-(4-aminobenzoyl)-β-alanine intermediate to sulfonate salt, b. converting the sulfonate salt to a diazoniumbenzoyl sulfonate salt, c. converting salt to Balsalazide disodium salt in solution, d. acidifying the solution to allow isolation of Balsalazide, e. optionally converting Balsalazide to pharmaceutically acceptable salt; and f. recovering same.

Surprisingly, sulfonic acids including alkyl and aryl sulfonic acids, such as methanesulfonic acid, ethanesulfonic acid p-toluenesulfonic acid, and benzenesulfonic acid, especially methanesulfonic acid, formed suitable intermediates which are more soluble in water thus forming aqueous solutions wherein the salt was soluble in water at temperatures below 15° C. (for example as depicted in FIG. 1). This latter temperature was selected as it provided for optimal reaction.

Additionally, the unexpectedly high water solubility of the sulfonic acid salts, such as the methanesulfonic acid salt, minimized the potential safety hazard associated with the diazotation reaction.

A preferred stoichiometric ratio of the sulfonic acid and the N-(4-aminobenzoyl)-β-alanine substrate was between about 2:1 to about 3.5:1. The most preferred stoichiometric ratio was about 2:1 to about 3.1:1. The diazonium salt reaction may be performed at a temperature of between about 0° C. to less than about 25° C., more preferably at about 5° C. to about 15° C., even more preferably at about 7° C. to about 12° C.

The selection of the operating temperature was chosen having regard to the decomposition of the diazonium intermediate which may start at a temperature as low as 25° C. This was evident from the decomposition experiments accomplished by us using, for instance Reactive Systems Screening Tool (RSST), where different reaction temperatures were selected as depicted in FIG. 1. The decomposition of the intermediate was indicated by the pressure increase.

Thus preventing this decomposition enhances the reaction since the decomposition energies—as measured by DSC—for the solid diazonium mesylate relative to the diazonium mesylate in solution were significant (almost ten-fold higher) as evidenced in FIG. 2.

Also as illustrated in FIG. 3, higher concentrations of sulfonic acid led to a decrease in the solubility of the β-alanine substrate. The preferred concentration of the aqueous sulfonic acid solution was about 4% to about 14%, more preferably about 7% to about 12%, and most preferably about 9%. The fact that higher concentrations were preferred, despite the decreased solubility of the salt, was a consequence of the fact that operationally, the use of about 9% sulfonic acid concentrations permitted proportionally lower reaction volumes, without compromising safety, and was advantageous for commercial scale-up.

According to another aspect, by carrying out a continuous process, the total amounts of diazonium intermediate present at any moment is significantly decreased.

Thus, according to an aspect of the invention, a preferred process proceeds through the following reactions:

a. the intermediate N-(4-aminobenzoyl)-β-alanine is converted to N-(4-ammoniumbenzoyl)-β-alanine sulfonate salt using a sulfonic acid in water, b. the N-(4-ammoniumbenzoyl)-β-alanine sulfonate salt is treated with aqueous sodium nitrite solution at low temperature to generate N-(4-diazoniumbenzoyl)-β-alanine sulfonate salt, c. the aqueous solution obtained is quenched with aqueous disodium salicylate to furnish Balsalazide disodium solution, d. the solution is acidified to allow isolation of Balsalazide, and e. optionally converting the Balsalazide to a pharmaceutically acceptable salt (such as disodium salt).

DETAILED DESCRIPTION OF EXAMPLES EMBODYING THE INVENTION

Example 1

Batch Process

Figure 1:
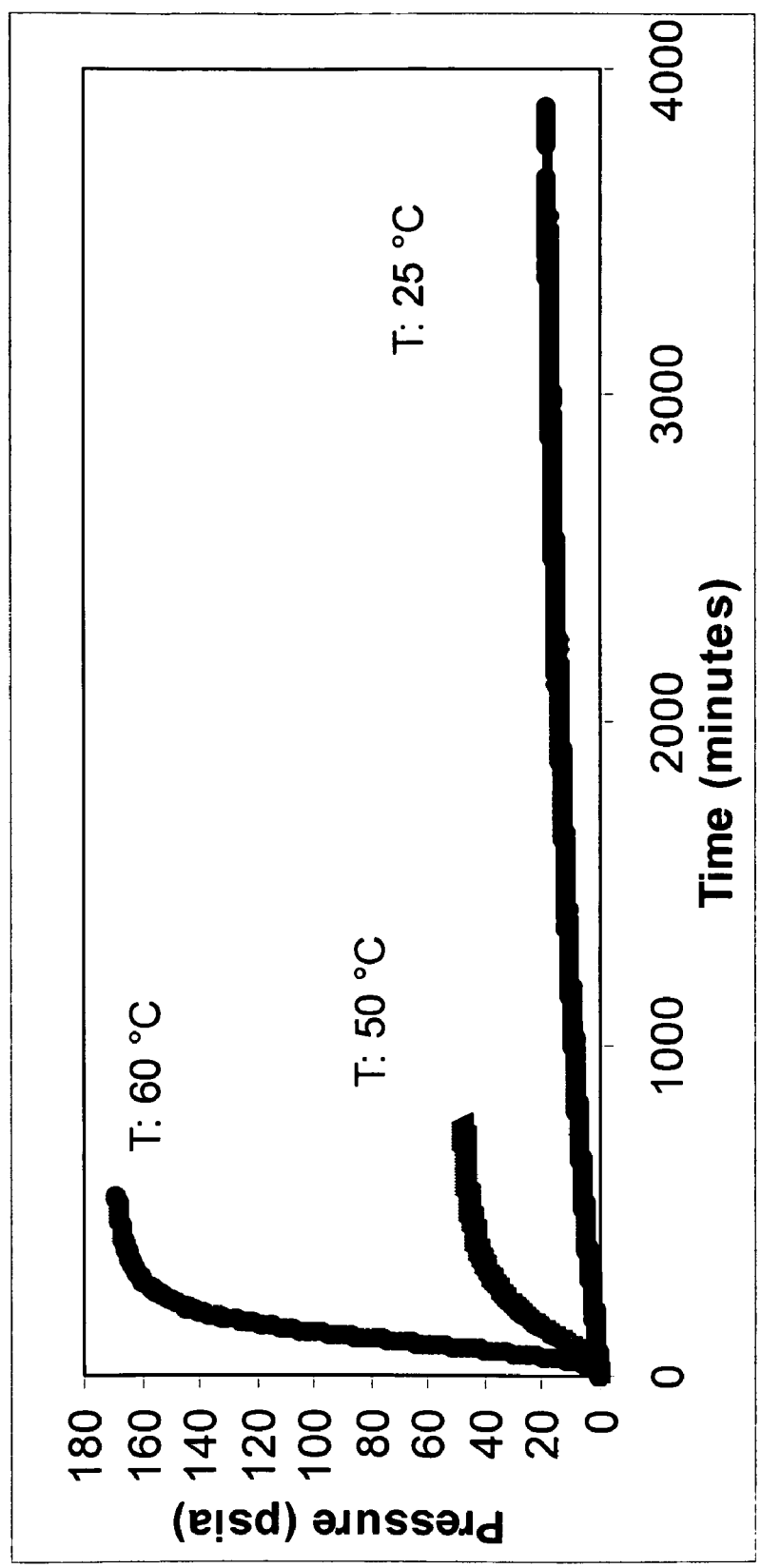
FIG. 1—Plot showing the rate of decomposition of diazonium mesylate at different temperatures. Increased pressure is indicative of the decomposition of the mesylate to form nitrogen gas.
Figure 2:
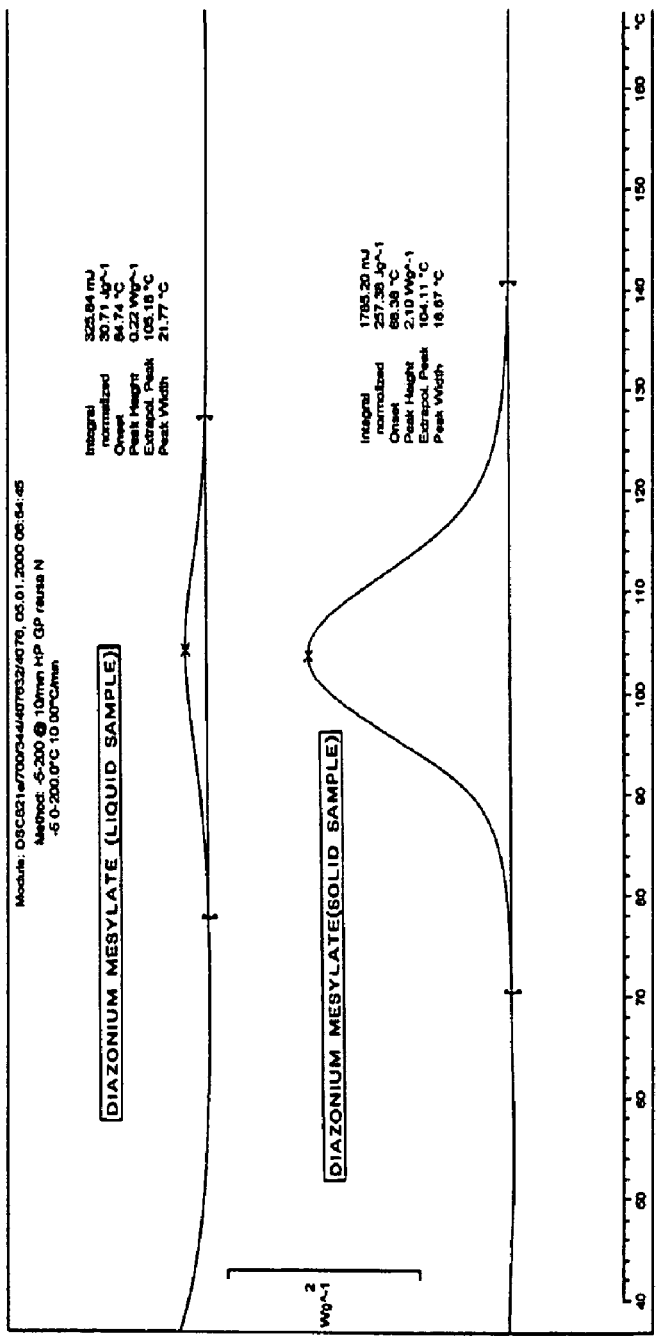
FIG. 2—A DSC plot of liquid and solid diazonium mesylate. The decomposition energy of the solid form of diazonium mesylate is greater than that of the diazonium mesylate in solution.
Figure 3:
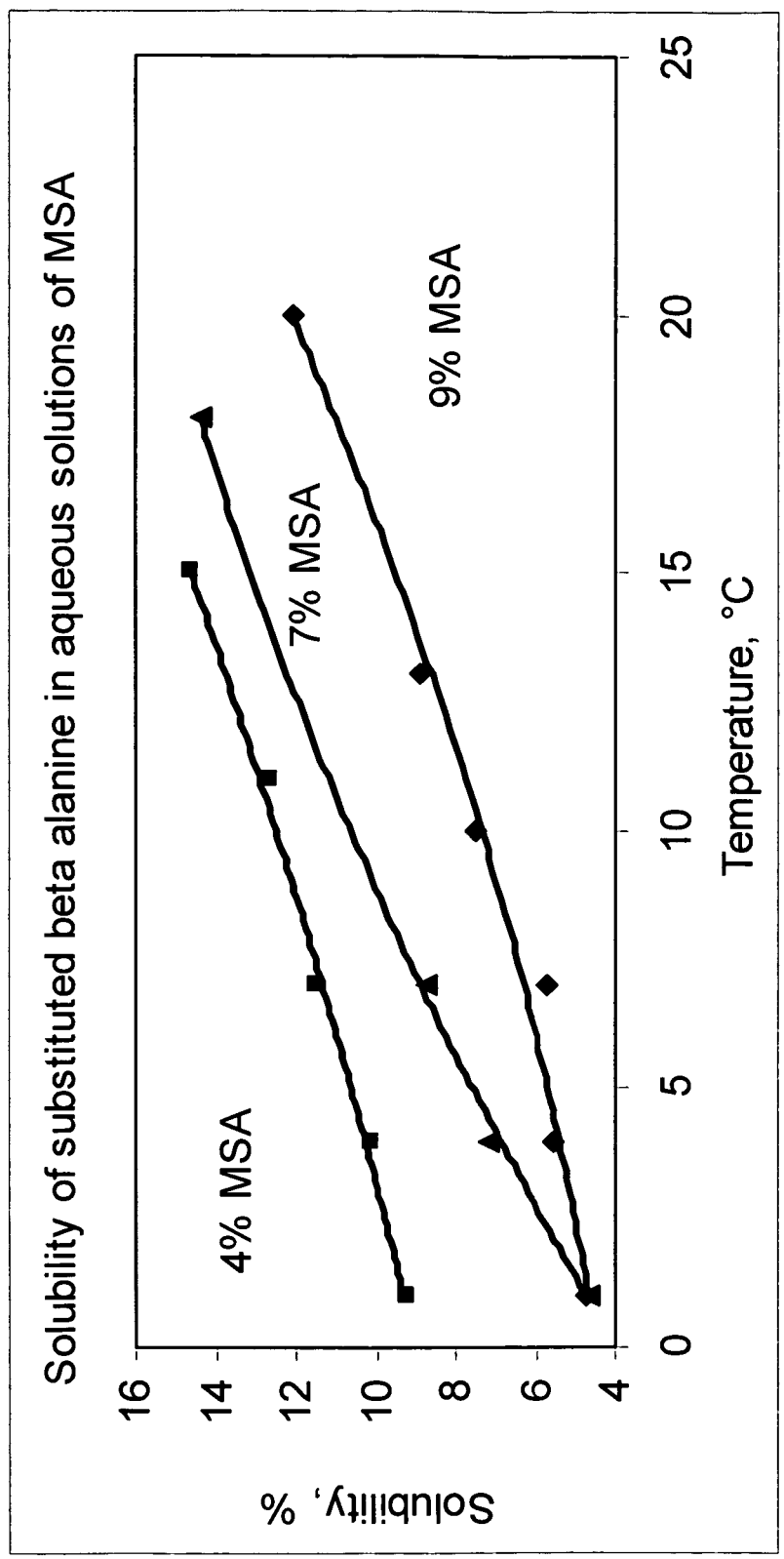
FIG. 3—A comparison of the relative solubility of mesylate in differing concentrations of aqueous methanesulfonic acid.

N-(4-Aminobenzoyl)-β-alanine (100 g) was suspended in water (1300 mL) and methanesulfonic acid (115.4 g) was added to this mixture. The mixture was cooled to 10° C. and a solution of sodium nitrite (34.46 g) in water (200 mL) was added at a rate such that the temperature stayed below 12° C. The mixture was stirred for 30 min and added to an ice-cold solution of salicylic acid (69.65 g), sodium hydroxide (40.35 g) and sodium carbonate (106.9 g) in 1 L water at 7-12° C. After 3 hours at 10° C., the mixture was heated to 60-65° C. and acidified to pH 4.0-4.5 by the addition of hydrochloric acid. After a further 3 hours at 60-65° C., the mixture was cooled to ambient temperature, filtered, washed with water and dried in vacuo to yield Balsalazide. Yield ca. 90%. Balsalazide was transformed into its disodium salt in ca. 85% yield by treatment with aqueous NaOH solution followed by crystallization from n-propanol/methanol.

$^1$H-NMR (400 MHz; $D_2O$): δ=8.04 ppm (s); 7.67 ppm (d; J=8.2 Hz); 7.62 ppm (d, J=9.2 Hz); 7.53 ppm (d; J=8.2 Hz); 6.84 ppm (d; J=8.9 Hz); 3.57 ppm (t, J=7.1 Hz); 2.53 ppm (t; J=7.2 Hz).

Example 2

Continuous Process

Figure 4:
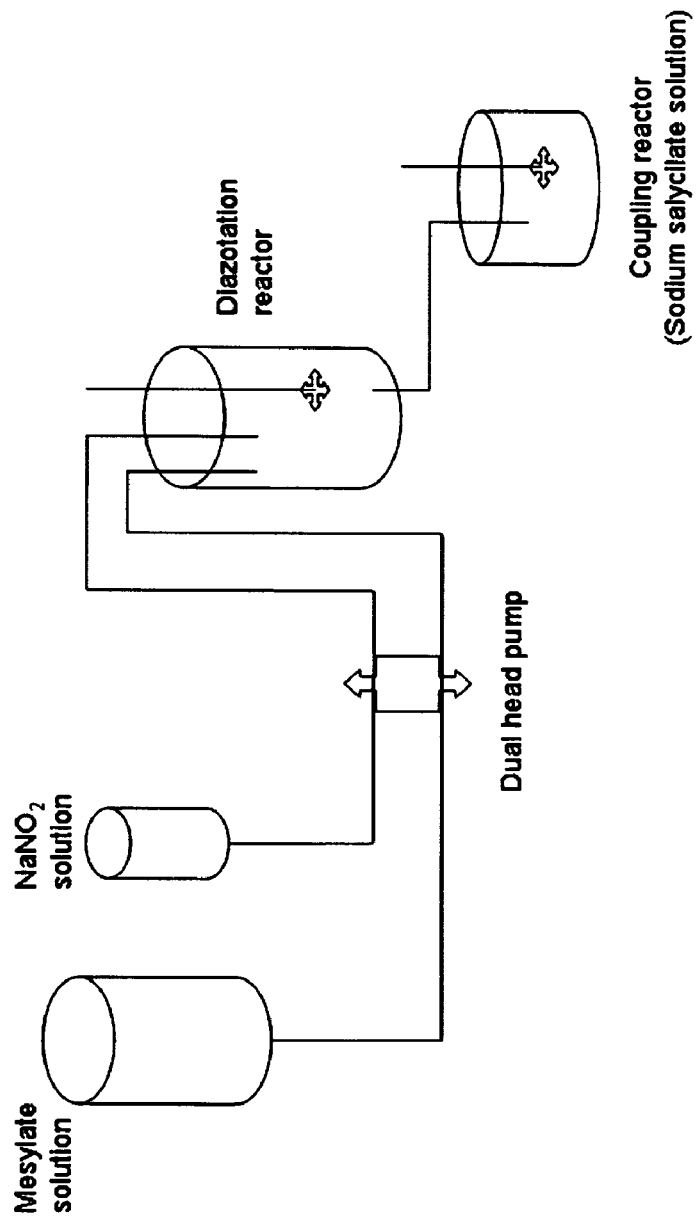
FIG. 4—A diagram of the flow reactor system for the diazotation and coupling reactions.

For the continuous operation, a conventional dual-head metering pump (Ratiomatic by FMI) was used to deliver the mesylate solution and the aqueous sodium nitrite solution. The schematic diagram shown in FIG. 4 represents a set-up used for the continuous process. The first pump-head was set at 13.9 g/min whereas the second was set at 2.1 g/min. These flow rates offered a residence time of 9.4 min. The yield of the coupled intermediate from this residence time was 93%. The working solutions were prepared as follow:

The mesylate solution was prepared by the addition into a 2 L 3-necked round bottom flask, of N-(4-aminobenzoyl) β-alanine (120 g) followed by of DI water (1560 g) and methanesulfonic acid (177.5 g) (Batch appearance: clear solution). The first pump-head was primed with this solution and the flow rate was adjusted to 13.9 g/min.

The sodium nitrite solution was prepared by dissolving of sodium nitrite (41.8 g) in of DI water (240 g) (Batch appearance: clear solution). The second pump-head was primed with this solution and the flow rate adjusted to 2.1 g/min.

The quenching solution (sodium salicylate) was made by adding salicylic acid (139.3 g) to DI water (900 g) followed by of sodium carbonate (106.9 g) and 50% aqueous sodium hydroxide (80 g).

The diazotation reaction was performed in a 500 ml jacketed flow reactor with a bottom drain valve. The drain valve was set at 16 g/min. For reactor start-up, the flow reactor was charged with 150 mL of DI water as a working volume and cooled to the reactions initial temperature of 0-5° C. Concomitantly, the additions of the mesylate and sodium nitrite solutions were started and the bottom valve of the flow reactor was opened. During the diazotization, the flow rate of both solutions remained fixed and the temperature was kept below 12° C. and at the end of additions the pumps were stopped while the remaining contents in the flow reactor were drained into the quenching salicylic acid solution. Analysis of the contents in the quenching reactor indicated no signs of uncoupled starting material (diazonium compound). The reactor contents were heated to 60-65° C. for 2-3 hrs before adjusting the pH to precipitate the coupling product. This provided 191.5 g of product.

While the foregoing provides a detailed description of a preferred embodiment of the invention, it is to be understood that this description is illustrative only of the principles of the invention and not limitative. Furthermore, as many changes can be made to the invention without departing from the scope of the invention, it is intended that all material contained herein be interpreted as illustrative of the invention and not in a limiting sense.

The invention claimed is:

1. A process for the preparation of Balsalazide and its pharmaceutically acceptable salts wherein the reaction comprises:
   a. the intermediate N-(4-aminobenzoyl)-β-alanine is converted to N-(4-ammoniumbenzoyl)-β-alanine sulfonate salt using a sulfonic acid in water,
   b. the N-(4-ammoniumbenzoyl)-β-alanine sulfonate salt is treated with aqueous sodium nitrite solution at low temperature to generate N-(4-diazoniumbenzoyl)-β-alanine sulfonate salt,
   c. the aqueous solution obtained is quenched with aqueous disodium salicylate to furnish Balsalazide disodium solution,
   d. the solution is acidified to allow isolation of Balsalazide, and
   e. optionally converting the Balsalazide to a pharmaceutically acceptable salt (such as disodium salt).

2. A process for the preparation of Balsalazide and its pharmaceutically acceptable salts wherein the reaction comprises:
   a. converting N-(4-aminobenzoyl)-β-alanine intermediate to sulfonate salt,
   b. converting the sulfonate salt to a diazoniumbenzoyl sulfonate salt,
   c. converting salt to Balsalazide disodium salt in solution,
   d. acidifying the solution to allow isolation of Balsalazide,
   e. optionally converting Balsalazide to pharmaceutically acceptable salt, and
   f. recovering same.

3. A process for the preparation of Balsalazide and its pharmaceutically acceptable salts using sulfonic acids in water during the diazotation reaction of N-(4-ammoniumbenzoyl)-β-alanine sulfonate salt wherein the reaction comprises:
   a. the intermediate N-(4-aminobenzoyl)-β-alanine is converted to N-(4-ammoniumbenzoyl)-β-alanine sulfonate salt using a sulfonic acid in water,
   b. the N-(4-ammoniumbenzoyl)-β-alanine sulfonate salt is treated with aqueous sodium nitrite solution at low temperature to generate N-(4-diazoniumbenzoyl)-β-alanine sulfonate salt,
   c. the aqueous solution obtained is quenched with aqueous disodium salicylate to furnish Balsalazide disodium solution,
   d. the solution is acidified to allow isolation of Balsalazide, and
   e. optionally converting the Balsalazide to a pharmaceutically acceptable salt (such as disodium salt).

4. A process according to claim 1, 2 or 3 where the sulfonic acid is methanesulfonic acid.

5. A process according to claim 1, 2 or 3 where the sulfonic acid is p-toluenesulfonic acid.

6. A process according to claim 1, 2 or 3 where the diazonium salt forming reaction is carried out temperatures between 0° C. and 25° C.

7. The process according to claim 1, 2, or 3 where the reaction is carried out at temperatures between 7° C. and 12° C.

8. The process of claim 1, 2 or 3 wherein the stoichiometry of the sulfonic acid to the N-(4-aminobenzoyl-β-alanine substrate was 2:1 to 3.5:1.

9. The process of claim 1, 2 or 3 wherein the stoichiometry of the sulfonic acid to the N-(4-aminobenzoyl)-β-alanine substrate was 2:1 to 3.1:1.

10. A continuous process for the preparation of Balsalazide and its pharmaceutically acceptable salts wherein the reaction comprises:
   a. the intermediate N-(4-aminobenzoyl)-β-alanine is converted to N-(4-ammoniumbenzoyl)-β-alanine sulfonate salt using a sulfonic acid in water,
   b. the N-(4-ammoniumbenzoyl)-β-alanine sulfonate salt is treated with aqueous sodium nitrite solution at low temperature to generate N-(4-diazoniumbenzoyl)-β-alanine sulfonate salt,
   c. the aqueous solution obtained is quenched with aqueous disodium salicylate to furnish Balsalazide disodium solution,
   d. the solution is acidified to allow isolation of Balsalazide, and e. optionally converting the Balsalazide to a pharmaceutically acceptable salt (such as disodium salt).

11. A continuous process for the preparation of Balsalazide and its pharmaceutically acceptable salts wherein the reaction comprises:
   a. converting N-(4-aminobenzoyl)-β-alanine intermediate to sulfonate salt,
   b. converting the sulfonate salt to a diazoniumbenzoyl sulfonate salt,
   c. converting salt to Balsalazide disodium salt in solution,
   d. acidifying the solution to allow isolation of Balsalazide,
   e. optionally converting Balsalazide to pharmaceutically acceptable salt, and
   f. recovering same.

12. A continuous process for the preparation of Balsalazide and its pharmaceutically acceptable salts using sulfonic acid salts in water wherein the reaction comprises:
   a. the intermediate N-(4-aminobenzoyl)-β-alanine is converted to N-(4-ammoniumbenzoyl)-β-alanine sulfonate salt using a sulfonic acid in water,
   b. the N-(4-ammoniumbenzoyl)-β-alanine sulfonate salt is treated with aqueous sodium nitrite solution at low temperature to generate N-(4-diazoniumbenzoyl)-β-alanine sulfonate salt,
   c. the aqueous solution obtained is quenched with aqueous disodium salicylate to furnish Balsalazide disodium solution,
   d. the solution is acidified to allow isolation of Balsalazide, and
   e. optionally converting the Balsalazide to a pharmaceutically acceptable salt (such as disodium salt).

13. A process for the preparation of Balsalazide and its pharmaceutically acceptable salts according to claim 10, 11 or 12 where the stoichiometry of the sulfonic acid to the N-(4-aminobenzoyl)-β-alanine substrate was 2:1 to 3.5:1.

14. A process for the preparation of Balsalazide and its pharmaceutically acceptable salts according to claim 10, 11 or 12 where the stoichiometry of the sulfonic acid to the N-(4-aminobenzoyl)-β-alanine substrate was 2:1 to 3.1:1.

15. A process for the preparation of Balsalazide and its pharmaceutically acceptable salts according to claim 10, 11 or 12 where the concentration of the aqueous sulfonic acid solution was 4% to 14%.

16. A process for the preparation of Balsalazide and its pharmaceutically acceptable salts according to claim 10, 11 or 12 where the concentration of the aqueous sulfonic acid solution was 7% to 12%.

17. A process for the preparation of Balsalazide and its pharmaceutically acceptable salts according to claim 10, 11 or 12 where the concentration of the aqueous sulfonic acid solution was about 9%.

18. N-(4-diazoniumbenzoyl)-β-alanine methanesulfonate.

19. N-(4-diazoniumbenzoyl)-β-alanine p-toluenesulfonate.

* * * * *